(12) United States Patent
Zhan et al.

(10) Patent No.: US 8,884,091 B2
(45) Date of Patent: Nov. 11, 2014

(54) INTEGRATION OF HYDRO-DECHLORINATION AND HYDRO-REGENERATION

(71) Applicants: Bi-Zeng Zhan, Albany, CA (US); Thomas Van Harris, Benicia, CA (US); Hye Kyung Cho Timken, Albany, CA (US)

(72) Inventors: Bi-Zeng Zhan, Albany, CA (US); Thomas Van Harris, Benicia, CA (US); Hye Kyung Cho Timken, Albany, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 103 days.

(21) Appl. No.: 13/829,620

(22) Filed: Mar. 14, 2013

(65) Prior Publication Data

US 2014/0275680 A1    Sep. 18, 2014

(51) Int. Cl.
  *C07C 2/60* (2006.01)
  *C07C 2/62* (2006.01)
  *C07C 2/58* (2006.01)

(52) U.S. Cl.
  CPC ........................................ *C07C 2/58* (2013.01)
  USPC ............ 585/712; 585/727; 585/728; 585/729

(58) Field of Classification Search
  CPC .................................. C07C 2/60; C07C 2/62
  USPC ................................ 585/712, 727, 728, 729
  See application file for complete search history.

(56) References Cited

U.S. PATENT DOCUMENTS

| | | | |
|---|---|---|---|
| 7,432,408 B2 | 10/2008 | Timken et al. | |
| 7,495,144 B2 | 2/2009 | Elomari | |
| 7,651,970 B2 | 1/2010 | Elomari et al. | |
| 7,678,727 B2 | 3/2010 | Harris et al. | |
| 7,691,771 B2 | 4/2010 | Harris et al. | |
| 7,825,055 B2 | 11/2010 | Elomari et al. | |
| 2007/0142215 A1 | 6/2007 | Harris et al. | |
| 2010/0298620 A1 | 11/2010 | Hommeltoft | |
| 2011/0155640 A1 | 6/2011 | Timken et al. | |
| 2011/0230692 A1 | 9/2011 | Timken et al. | |
| 2011/0319694 A1 | 12/2011 | Timken et al. | |
| 2012/0024750 A1 | 2/2012 | Zhan et al. | |
| 2013/0001133 A1 | 1/2013 | Zhan et al. | |

OTHER PUBLICATIONS

U.S. Appl. No. 13/563,385, filed Jul. 31, 2012, 25 pages.
U.S. Appl. No. 13/563,355, filed Jul. 31, 2012, 29 pages.
PCT/US2013/071273, Notification of Transmittal of the International Search Report and the Written Opinion of the International Searching Authority, or the Declaration, Mail date Mar. 19, 2014, 34 pages.

*Primary Examiner* — Thuan D Dang
(74) *Attorney, Agent, or Firm* — Susan M. Abernathy

(57) ABSTRACT

We provide an integrated process to produce alkylate gasoline, comprising:
  a. alkylating a mixture of hydrocarbons using a chloride-containing ionic liquid catalyst in an alkylation reactor to produce an alkylate gasoline comprising a chloride contaminant;
  b. hydro-regenerating the chloride-containing ionic liquid catalyst in a hydrogenation reactor;
  c. hydro-dechlorinating the alkylate gasoline comprising the chloride contaminant in a dechlorination reactor at a dechlorination pressure from 0 to 1000 psig of a hydrogenation pressure used in the hydrogenation reactor, to produce a dechlorinated alkylate gasoline; and
  d. feeding an off-gas, comprising 70 to 99.9 vol % hydrogen, from the dechlorination reactor to the hydrogenation reactor. We also provide an integrated alkylation process unit for conducting this process.

16 Claims, 1 Drawing Sheet

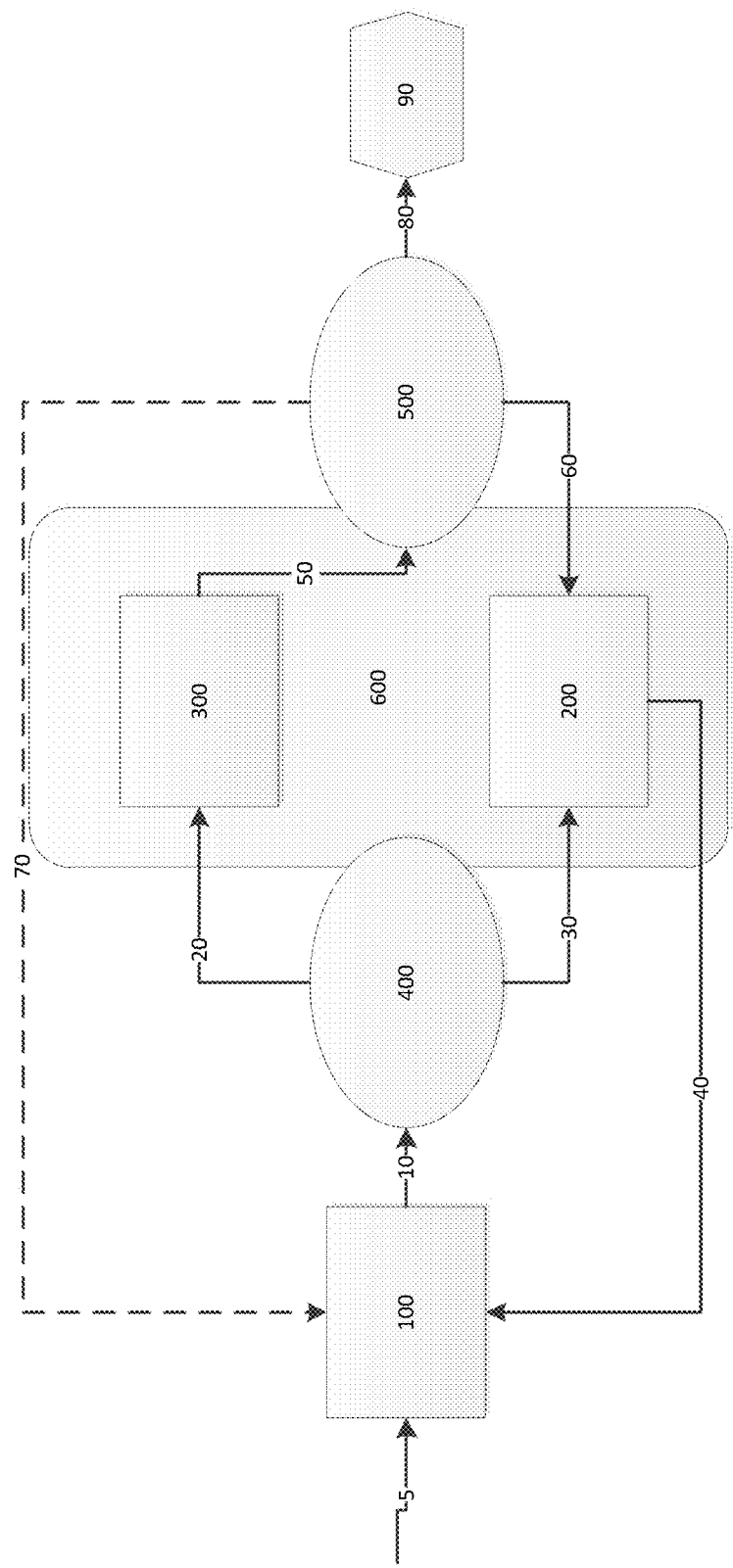

INTEGRATION OF HYDRO-DECHLORINATION AND HYDRO-REGENERATION

TECHNICAL FIELD

This application is directed to an integrated process to produce alkylate gasoline. The process comprises both hydro-regenerating and hydro-dechlorinating. This application is also directed to an integrated alkylation process unit for performing this process.

BACKGROUND

Improved integration processes to produce high quality alkylate gasoline with low chloride content are needed.

SUMMARY

This application provides an integrated process to produce alkylate gasoline, comprising:
 a. alkylating a mixture of hydrocarbons using a chloride-containing ionic liquid catalyst in an alkylation reactor to produce an alkylate gasoline comprising a chloride contaminant;
 b. hydro-regenerating the chloride-containing ionic liquid catalyst in a hydrogenation reactor;
 c. hydro-dechlorinating the alkylate gasoline comprising the chloride contaminant in a dechlorination reactor at a dechlorination pressure from 0 to 1000 psig of a hydrogenation pressure used in the hydrogenation reactor, to produce a dechlorinated alkylate gasoline; and
 d. feeding an off-gas, comprising 70 to 99.9 vol % hydrogen, from the dechlorination reactor to the hydrogenation reactor.

This application also provides an integrated alkylation process unit, comprising:
 a. an alkylation reactor comprising a chloride-containing ionic liquid catalyst that produces an alkylate gasoline comprising a chloride contaminant;
 b. a hydrogenation reactor that receives a used chloride-containing ionic liquid catalyst from the alkylation reactor and regenerates the chloride-containing ionic liquid catalyst;
 c. a dechlorination reactor that hydro-dechlorinates the alkylate gasoline at a pressure from 0 to 1000 psig of a hydrogenation pressure used in the hydrogenation reactor, to produce a dechlorinated alkylate gasoline; and
 d. a connection between the hydrogenation reactor and the dechlorination reactor that feeds an off-gas comprising from 70-99.9 vol % hydrogen from the dechlorination reactor to the hydrogenation reactor.

BRIEF DESCRIPTION OF THE DRAWINGS

FIG. 1 is a diagram of an integrated alkylation process unit used to make high quality alkylate gasoline.

DETAILED DESCRIPTION

Description of FIG. 1

One embodiment of how this method can be practiced is shown in FIG. 1. A mixture of hydrocarbons (5) is fed to an alkylation reactor (100). The alkylation reactor effluent (10) is fed to a liquid/liquid separator (400). The liquid/liquid separator (400) separates the alkylation reactor effluent (10) into an alkylate gasoline comprising a chloride contaminant (20) and a chloride-containing ionic liquid catalyst (30). The alkylate gasoline comprising a chloride contaminant (20) is fed to a dechlorination reactor (300). The chloride-containing ionic liquid catalyst is fed to a hydrogenation reactor (200). A regenerated ionic liquid catalyst (40) from the hydrogenation reactor (200) is fed to the alkylation reactor (100). The dechlorination reactor (300) and the hydrogenation reactor (200) are in a single pressurized zone (600). The dechlorination reactor effluent (50) is fed to a gas/liquid separator (500). The gas/liquid separator (500) separates the dechlorination reactor effluent (50) into HCl (70), a separated liquid (80) and an off-gas (60). The off-gas (60) comprises hydrogen and is fed to the hydrogenation reactor (200). The HCl (70) is fed to the alkylation reactor (100). The separated liquid (80) comprises a dechlorinated alkylate gasoline (90).

Alkylating

The alkylating of the mixture of hydrocarbons is performed in an alkylation reactor under conditions known to produce alkylate gasoline. The alkylation conditions in the alkylation reactor are selected to provide the desired product yields and quality. The alkylation reaction in the alkylation reactor is generally carried out in a liquid hydrocarbon phase, in a batch system, a semi-batch system, or a continuous system. Catalyst volume in the alkylation reactor is in the range of 1 vol % to 80 vol %, for example from 2 vol % to 70 vol %, from 3 vol % to 50 vol %, or from 5 vol % to 25 vol %. In some embodiments, vigorous mixing can be used to provide good contact between the reactants and the catalyst. The alkylation reaction temperature can be in the range from $-40°$ C. to $150°$ C., such as $-20°$ C. to $100°$ C., or $-15°$ C. to $50°$ C. The pressure can be in the range from atmospheric pressure to 8000 kPa. In one embodiment the pressure is kept at a high enough level to keep the reactants in the liquid phase. The residence time of reactants in the reactor can be in the range of a second to 60 hours.

In one embodiment, the molar ratio of isoparaffin to olefin in the alkylation reactor can vary over a broad range. Generally the molar ratio of isoparaffin to olefin is in the range of from 0.5:1 to 100:1. For example, in different embodiments the molar ratio of isoparaffin to olefin is from 1:1 to 50:1, 1.1:1 to 10:1, or 1.1:1 to 20:1. Lower isoparaffin to olefin molar ratios will tend to produce a higher yield of higher molecular weight alkylate products, and thus can be selected when operating the alkylation reactor in a distillate mode, such as described in US20110230692A1.

Chloride-Containing Ionic Liquid Catalyst

The alkylation catalyst used in the alkylation reactor is a chloride-containing ionic liquid catalyst.

The chloride-containing ionic liquid catalyst is composed of at least two components which form a complex. The chloride-containing ionic liquid catalyst comprises a first component and a second component. The first component of the chloride-containing ionic liquid catalyst can comprise a Lewis Acid selected from components such as Lewis Acidic compounds of Group 13 metals, including aluminum halides, alkyl aluminum halide, gallium halide, and alkyl gallium halide (see International Union of Pure and Applied Chemistry (IUPAC), version 3, October 2005, for Group 13 metals of the periodic table). Other Lewis Acidic compounds, in addition to those of Group 13 metals, can also be used. In one embodiment the first component is aluminum halide or alkyl aluminum halide. For example, aluminum trichloride can be the first component of the chloride-containing ionic liquid catalyst.

The second component making up the chloride-containing ionic liquid catalyst is an organic salt or mixture of salts. These salts can be characterized by the general formula Q+A−, wherein Q+ is an ammonium, phosphonium, boronium, iodonium, or sulfonium cation and A− is a negatively charged ion such as Cl−, Br−, ClO4−, NO$_3$−, BF$_4$−, BCl4−, PF6−, SbF6−, AlCl4−, TaF6−, CuCl2−, FeCl3−, HSO3−, RSO3−, SO3CF3−, and 3-sulfurtrioxyphenyl. In one embodiment the second component is selected from those having quaternary ammonium halides containing one or more alkyl moieties having from about 1 to about 12 carbon atoms, such as, for example, trimethylamine hydrochloride, methyltributylammonium halide, or substituted heterocyclic ammonium halide compounds, such as hydrocarbyl substituted pyridinium halide compounds for example 1-butylpyridinium halide, benzylpyridinium halide, or hydrocarbyl substituted imidazolium halides, such as for example, 1-ethyl-3-methyl-imidazolium chloride.

In one embodiment the chloride-containing ionic liquid catalyst is selected from the group consisting of hydrocarbyl substituted pyridinium chloroaluminate, hydrocarbyl substituted imidazolium chloroaluminate, quaternary amine chloroaluminate, trialkyl amine hydrogen chloride chloroaluminate, alkyl pyridine hydrogen chloride chloroaluminate, and mixtures thereof. For example, the chloride-containing ionic liquid catalyst can be an acidic haloaluminate ionic liquid, such as an alkyl substituted pyridinium chloroaluminate or an alkyl substituted imidazolium chloroaluminate of the general formulas A and B, respectively.

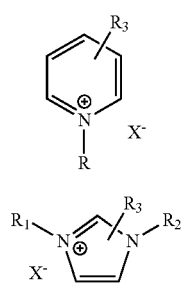

In the formulas A and B; R, R1, R2, and R3 are H, methyl, ethyl, propyl, butyl, pentyl or hexyl group, X is a chloroaluminate. In the formulas A and B, R, R1, R2, and R3 may or may not be the same. In one embodiment the chloride-containing ionic liquid catalyst is N-butylpyridinium chloroaluminate. Examples of highly acidic chloroaluminates are $Al_2Cl_7^-$ and $Al_3Cl_{10}^-$.

In another embodiment the chloride-containing ionic liquid catalyst can have the general formula RR'R"NH+$Al_2Cl_2^-$, wherein N is a nitrogen containing group, and wherein RR' and R" are alkyl groups containing 1 to 12 carbons, and where RR' and R" may or may not be the same.

The presence of the first component should give the chloride-containing ionic liquid a Lewis or Franklin acidic character. Generally, the greater the mole ratio of the first component to the second component, the greater is the acidity of the chloride-containing ionic liquid catalyst.

In one embodiment, the chloride-containing ionic liquid catalyst is mixed in the alkylation reactor with a hydrogen halide or an organic halide. The hydrogen halide or organic halide can boost the overall acidity and change the selectivity of the chloride-containing ionic liquid catalyst. The organic halide can be an alkyl halide. The alkyl halides that can be used include alkyl bromides, alkyl chlorides, alkyl iodides, and mixtures thereof. A variety of alkyl halides can be used. Alkyl halide derivatives of the isoparaffins or the olefins that comprise the feed streams in the alkylation process are good choices. Such alkyl halides include, but are not limited to, isopentyl halides, isobutyl halides, butyl halides (e.g., 1-butyl halide or 2-butyl halide), propyl halides and ethyl halides. Other alkyl chlorides or halides having from 1 to 8 carbon atoms can be also used. The alkyl halides can be used alone or in combination. The use of alkyl halides to promote hydrocarbon conversion by chloride-containing ionic liquid catalysts is taught in U.S. Pat. No. 7,495,144 and in U.S. Patent Publication No. US20100298620A1.

It is believed that the alkyl halide decomposes under hydrocarbon conversion conditions to liberate Bronsted acids or hydrogen halides, such as hydrochloric acid (HCl) or hydrobromic acid (HBr). These Bronsted acids or hydrogen halides promote the hydrocarbon conversion reaction. In one embodiment the halide in the hydrogen halide or alkyl halide is the same as a halide component of the chloride-containing ionic liquid catalyst. In one embodiment the alkyl halide is an alkyl chloride, for example t-butyl chloride. A hydrogen chloride or an alkyl chloride can be used advantageously, for example, when the chloride-containing ionic liquid catalyst is a chloroaluminate.

Hydro-Regenerating

The chloride-containing ionic liquid catalyst is hydro-regenerated in a hydrogenation reactor. The hydro-regeneration removes the impurities, such as conjunct polymer, from a used chloride-containing ionic liquid catalyst, thus increasing the acidity and ability of the catalyst to perform alkylations. The hydrogenation reactor contacts the used catalyst with hydrogen and typically, a hydrogenation catalyst to regenerate the chloride-containing ionic liquid catalyst.

In one embodiment, zeolites or molecular sieves are added to a hydrogenation catalyst in the hydrogenation reactor to improve the hydrogenation catalyst's performance. In one embodiment, the hydrogenation catalyst is supported. Typical support materials for the hydrogenation catalyst are kieselguhr, alumina, silica, and silica-alumina. Other support materials include alumina-boria, silica-alumina-magnesia, silica-alumina-titania and materials obtained by adding zeolites and other complex oxides thereto. When used, the support material has adequate mechanical strength and chemical stability at the hydrogenation reaction temperature.

In one embodiment, the hydrogenation is carried out in the presence of a catalyst which usually comprises a metal or non metal hydrogenation component on a porous support material, such as a natural clay or a synthetic oxide. Examples of metal hydrogenation components that can be used are Fe, Co, Ni, Ru, Rh, Pd, Pt, Ir, Os, Cr, Mn, Ti, V, Zr, Mo, W, and mixtures thereof. Examples of non metal hydrogenation components Te, As, and mixtures thereof. The hydrogenation components can be used singly or in combination. In one embodiment, the hydrogenation catalyst comprises Pt and Pd on an alumina support.

The hydrogenation can be carried out over a broad range of hydrogenation pressures, typically from about 50 to 3,400 psig. Hydrogenation conditions can include temperatures of −20° C. to 400° C., or 50° C. to 300° C. Hydrogenation contact times can be from 0.1 minute to 24 hours, such as 10 minutes to 12 hours. Feed to catalyst ratios during the hydrogenation can vary from 0.1 to 10 vol/vol/hour. A normal hydrocarbon can optionally be used as a solvent in the hydrogenation reactor.

Examples of hydrogenation of ionic liquid catalysts for regeneration, for example, are given in U.S. Pat. No. 7,691,771, U.S. Pat. No. 7,651,970, U.S. Pat. No. 7,678,727, U.S. Pat. No. 7,825,055, and U.S. patent application Ser. No. 13/563,385, filed Jul. 31, 2012.

Alkylate Gasoline Comprising a Chloride Contaminant

In one embodiment, the chloride contaminant in the alkylate gasoline can comprise one or more alkyl chlorides, e.g., a $C_2$-$C_{16}$ alkyl chloride. In one embodiment, the chloride contaminant comprises a C4+ organic chloride. In one embodiment, the alkylate gasoline feed to the dechlorination reactor may have an organic chloride content generally in the range from about 50 ppm to 5000 ppm, from about 100 ppm to 4000 ppm, or from about 200 ppm to 3000 ppm.

In one embodiment, the alkylate gasoline comprising a chloride contaminant has a C8 fraction with 70 to 90 wt % trimethylpentane (TMP). Trimethylpentane (TMP) is measured by gas chromatography.

Hydro-Dechlorinating

The hydro-dechlorinating of the alkylate gasoline comprising the chloride contaminant is performed at a dechlorination pressure from 10 to 2400 psig. For example, the dechlorination pressure can be from 10 to 1,000 psig or 30 to 600 psig. In one embodiment the dechlorination pressure is from 150 to 1500 psig. If the dechlorination pressure is greater than 1500 psig, then a high pressure vessel can be used. The hydro-dechlorinating is performed in a dechlorination reactor at a dechlorination pressure from 0 to 1000 psig of the hydrogenation pressure used in the hydrogenation reactor. Examples of hydro-dechlorination of alkylate gasoline are described in US20120024750 and US20130001133.

In one embodiment, the dechlorination pressure is within 500 psig of the hydrogenation pressure. In another embodiment the dechlorination pressure is within 10 to 1,000 psig of the hydrogenation pressure, such within 250 psig of the hydrogenation pressure.

In some embodiments, the dechlorination pressure is greater than the hydrogenation pressure, such as at least 20 or 30 psig above the hydrogenation pressure. In one embodiment, the dechlorination pressure is from 30 to 200 psig higher than the hydrogenation pressure. In another embodiment, the dechlorination pressure is from 50 to 175 psig higher than the hydrogenation pressure.

In one embodiment, the hydrogenation reactor and the dechlorination reactor are in a common pressurized zone in the integrated process. This can be advantageous, as common equipment can be used and there is reduced process complexity.

A dechlorination catalyst can be used to perform the hydro-dechlorination. The dechlorination catalyst may comprise a refractory oxide, such as silica, silica-alumina, alumina, zinc oxide, titania, zirconia, magnesium oxide, activated carbon, or a zeolite, and combinations thereof. In an embodiment, the dechlorination catalyst may consist essentially of alumina. In another embodiment, the dechlorination catalyst may comprise a zeolite. In one embodiment, the dechlorination catalyst comprises a metal or non metal hydrogenation component on a porous support material. Examples of metal hydrogenation components that can be used are Fe, Co, Ni, Ru, Rh, Pd, Pt, Ir, Os, Cr, Mn, Ti, V, Zr, Mo, W, and mixtures thereof. Examples of non metal hydrogenation components are Te, As, and mixtures thereof. The hydrogenation components can be used singly or in combination. In one embodiment, the dechlorination catalyst and the hydrogenation catalyst are the same. For example, both the dechlorination catalyst and the hydrogenation catalyst could comprise Pt and Pd on an alumina support.

In some embodiments, a guard bed can be used before the hydrogenation catalyst, the hydrodechlorination catalyst, or both, to protect them from contaminants that could be present in the feeds to these catalysts.

The conditions within the dechlorination reactor can comprise a dechlorination temperature generally in the range from about 40° F. (about 4.444 degree Celsius) to 700° F. (371.1 degree Celsius), typically from about 100° F. (about 37.78 degree Celsius) to 600° F. (315.6 degree Celsius), and often from about 200° F. (about 93.33 degree Celsius) to 500° F. (260 degree Celsius). In one embodiment, the temperature in the dechlorination reactor is from 300° F. (148.9 degree Celsius) to 600° F. (315.6 degree Celsius). A liquid hourly space velocity (LHSV) feed rate of the alkylate gasoline comprising the chloride contaminant to the dechlorination reactor can be in the range from about 0.1 to 50 hr$^{-1}$, or from about 0.5 to 20 hr$^{-1}$.

In one embodiment, the hydro-dechlorinating reduces a total halide from greater than 50 wppm in the alkylate gasoline comprising the chloride contaminant to less than 10 wppm in a dechlorinated alkylate gasoline. The total halide is measured by X-ray diffraction.

In one embodiment, the dechlorinated alkylate gasoline retains greater than 90 wt % of a TMP in the C8 fraction of the alkylate gasoline comprising the chloride contaminant. In another embodiment, the dechlorinated alkylate gasoline retains from 97 to 100 wt % of the TMP in the C8 fraction of the alkylate gasoline comprising the chloride contaminant.

Maintaining Dechlorination Temperature Below an Elevated Level

In one embodiment, it is preferable to maintain a temperature in the dechlorination reactor below an elevated temperature. An elevated temperature in the dechlorination reactor is defined herein as a temperature that causes a total chloride in the dechlorinated gasoline to increase above a lower level of total chloride that was obtained when hydro-dechlorinating at a temperature below the elevated temperature. In one embodiment, the elevated temperature causes a total chloride in the dechlorinated alkylate gasoline to be above 15 wppm, such as from 16 to 200 wppm. Examples of an elevated temperature in the dechlorination reactor, in the context of this disclosure, can be temperatures from 555° F. (290.6 degree Celsius) to 700° F. (371.1 degree Celsius), or 600° F. (315.6 degree Celsius) to 700° F. (371.1 degree Celsius).

HCl from Dechlorination

In one embodiment, an HCl is produced during the hydro-dechlorinating. The HCl may be generated from the chloride contaminant in the alkylate gasoline during dechlorination by hydro-dechlorination in the dechlorination reactor. In one embodiment, a carrier gas can promote catalytic dechlorination of the alkylate gasoline by flushing the HCl from the dechlorination reactor. The HCl that is produced during the hydro-dechlorinating can be recycled to the alkylation reactor.

In one embodiment, the HCl from the dechlorination reactor is mixed with a hydrogenation HCl from the hydrogenation reactor to make a mixed HCl feed that is recycled to the alkylation reactor. Processes for recycling HCl from a dechlorination reactor are taught in U.S. patent application Ser. No. 13/563,385, filed Jul. 31, 2012.

Off-Gas from the Dechlorination Reactor

An off-gas from the dechlorination reactor is fed to the hydrogenation reactor. The off-gas comprises greater than 50 vol % hydrogen. In one embodiment, it comprises from 70 to 99.9 vol % hydrogen. It can also contain a small amount of saturated light hydrocarbons and several hundreds of wppm of HCl. In one embodiment, the off-gas can also contain several thousands of wppm of HCl. For example, the off-gas can comprise from 100 to 50,000 wppm HCl. The off-gas is surprisingly useful as a source of the hydrogen to the hydrogenation reactor, and sometimes without requiring significant purification. In one embodiment, the off-gas requires no pretreatment before feeding to the hydrogenation reactor.

In one embodiment, the off-gas comprises from 90 to 99.9 vol % hydrogen. In one embodiment, the off-gas comprises small amounts of $C4^+$ and $C4^-$ hydrocarbons. For example the off-gas can comprise from 0.5 to 9.5 vol % C4+ hydrocarbons. In one embodiment, the off-gas comprises from 0.5 to 20 vol % $C4^-$ hydrocarbons. In one embodiment, the off-gas comprises from 0 to 0.05 vol C1-C3 hydrocarbons.

Integrated Alkylation Process Unit

The integrated alkylation process unit comprises an alkylation reactor, a hydrogenation reactor, and a dechlorination reactor as described above. There is a connection between the hydrogenation reactor and dechlorination reactor that feeds the off-gas comprising from 70-99.9 vol % hydrogen from the dechlorination reactor in the hydrogenation reactor.

In one embodiment, the process unit additionally comprises a recycle line from a gas/liquid separator that recycles a HCl from the dechlorination reactor to the alkylation reactor.

In another embodiment, the integrated alkylation process unit additionally comprises a pressurized zone comprising both the hydrogenation reactor and the dechlorination reactor. The pressurized zone comprising both reactors is possible because the pressure in the dechlorination reactor is from 0 to 1000 psig of a hydrogenation pressure used in the hydrogenation reactor.

EXAMPLES

Example 1

Ionic Liquid Catalyst Comprising Anhydrous Metal Chloride

Various ionic liquid catalysts made of metal chlorides such as $AlCl_3$, $GaCl_3$, and $InCl_3$ could be used in the alkylation process unit. N-butylpyridinium chloroaluminate ($C_5H_5C_4H_9Al_2Cl_7$) ionic liquid catalyst is an example used in our alkylation process units to make alkylate gasoline. The ionic liquid catalyst had the following composition:

| | |
|---|---|
| Wt % Al | 12.4 |
| Wt % Cl | 56.5 |
| Wt % C | 24.6 |
| Wt % H | 3.2 |
| Wt % N | 3.3 |

Example 2

Alkylation of $C_3/C_4$ Olefin and Isobutane to Make Alkylate Gasoline

Refinery isobutane containing 85% isobutane and 15% n-butane was used for this study. A refinery olefin stream containing $C_3$ and $C_4$ olefins ($C_3/C_4$ Olefin) from a Fluid Catalytic Cracking Unit (FCC unit) was dried with 13x molecular sieve and isomerized with a $Pd/Al_2O_3$ catalyst at 150° F., and 250 psig in the presence of hydrogen to produce isomerized $C_3$ and $C_4$ olefin feed with the composition shown in Table 1.

TABLE 1

Composition of Olefin Feed

| Composition | Mol % |
|---|---|
| Propane, C3 | 13.3 |
| Propylene, C3= | 25.4 |
| 1-Butene, 1-C4= | 2.3 |
| 2-Butene, 2-C4= | 16.2 |
| Isobutylene, i-C4= | 6.7 |
| n-Butane, nC4 | 12.4 |
| Isobutane, iC4 | 22.2 |
| C5+ | 1.6 |
| Sum | 100.0 |

Evaluation of $C_3/C_4$ olefins alkylation with isobutane was performed in a continuously stirred tank reactor. An 8:1 molar mixture of isobutane and olefin was fed to the reactor while vigorously stirring. An ionic liquid catalyst as described in Example 1 was fed to the reactor via a second inlet port targeted to occupy 6 vol % in the reactor. A small amount of n-butyl chloride was added to produce anhydrous HCl gas in situ. The average residence time in the reactor (combined volume of feeds and catalyst) was about 12 minutes. The outlet pressure was maintained at 170 psig and the reactor temperature was maintained at 95° F. (35° C.) using external cooling.

The reactor effluent was separated with a coalescing separator into a hydrocarbon phase and an ionic liquid catalyst phase. The hydrocarbon phase was further separated with three distillation columns into multiple streams, including: a gas stream containing $C_3^-$ fraction, an $nC_4$ stream, an $iC_4$ stream, and an alkylate stream. Alkylate Sample #1 was collected.

Example 3

Alkylation of $C_4$ Olefin and Isobutane to Make Alkylate Gasoline

Alkylate Sample #2 was produced using the same procedures of Example 2, except that the olefin feed source was a refinery $C_4$ olefin stream from a Fluid Catalytic Cracking Unit (FCC unit).

The two samples of alkylate were analyzed by Simulated Distillation, X-ray fluorescence (XRF), and gas chromatography (GC). The results are shown below:

TABLE 2

Properties of Alkylate Feed

| | Alkylate Sample #1 | Alkylate Sample #2 |
|---|---|---|
| Total Chlorides, wppm (XRF) | 455 | 760 |
| SimDist, Wt % | ° F. | |
| 0.50% | 27 | 32 |
| 5% | 74 | 144 |
| 10% | 131 | 174 |
| 30% | 192 | 205 |
| 50% | 204 | 227 |
| 70% | 234 | 237 |
| 90% | 328 | 311 |
| 95% | 360 | 363 |
| 99% | 454 | 421 |
| End Point | 502 | 450 |
| Wt % TMP in C8 (GC) | Not measured | 84.4 |

Example 4

Hydro-Dechlorination Catalyst

A lab-prepared Pt—Pd/Al$_2$O$_3$ catalyst was made from an alumina extrudate base via co-impregnation of chloroplatinic acid and palladium chloride in an HCl solution. The dechlorination catalyst contained 0.36 wt % Pd and 0.18 wt % Pt. The catalyst extrudates from the impregnation step were crushed to 24-42 mesh and loaded to the center of a ⅜" dechlorination reactor. Both the bottom and top zones of the dechlorination reactor were filled with 24 mesh silicon carbide. 2.765 g dry-weight of the dechlorination catalyst was loaded into the dechlorination reactor.

The dechlorination catalyst was activated by raising the temperature of the dechlorination reactor by 50° F./hr (27.78° C./hr) to 500° F. (260 degree Celsius), and holding the temperature at 500° F. (260 degree Celsius) (260 degree Celsius) (260 degree Celsius) (260 degree Celsius) for one hour, under flowing H$_2$ (100 cc/min) at 475 psig.

The Alkylate Sample #1 and Alkylate Sample #2 samples were filtered, then hydro-dechlorinated in the dechlorination reactor holding the activated dechlorination catalyst as described above.

Example 5

Treatment of Alkylate Sample #1 with Dechlorination Catalyst

The conditions in the dechlorination reactor were: 200 SCF/B (0.0356 m$^3$/L) H$_2$, from 5 LHSV, and 475 psig. The temperature in the dechlorination reactor was adjusted to different levels. The reactor effluent was separated with a gas-liquid separator into a hydrocarbon phase and a gas phase (off-gas). The results for the total chloride and wt % chloride removed in the dechlorinated product samples are shown below.

TABLE 3

Reduction of Chlorides in Alkylate

| Catalyst Temp. | LHSV | Total Chloride, wppm (XRF) | Wt % Chloride Removed |
|---|---|---|---|
| 360° F. (182.2 degree Celsius) | 5 | 103 | 77.4 |
| 380° F. (193.3 degree Celsius) | 5 | 48 | 89.3 |
| 400° F. (204.4 degree Celsius) | 5 | 0.5 | 99.9 |

Example 6

Treatment of Alkylate from Research Unit with Dechlorination Catalyst

The conditions in the dechlorination reactor were: 200 SCF/B (0.0356 m$^3$/L) H$_2$, 10 LHSV, and 475 psig. The temperature in the dechlorination reactor was adjusted to different levels, and the results for the wt % TMP in the C8 fractions, the total chloride, and wt % chloride removed in the dechlorinated product samples are shown below.

TABLE 4

Reduction of Chlorides in Alkylate

| Catalyst Temp. | LHSV | Wt % TMP in C8 (% Retained) | Total Chloride, wppm (XRF) | Wt % Chloride Removed |
|---|---|---|---|---|
| 440° F. (226.7 degree Celsius) | 10 | 84.1 (99.6) | 5.6 | 99.3 |
| 500° F. | 10 | 84.1 (99.6) | 6.1 | 99.2 |
| 550° F. (287.8 degree Celsius) | 10 | 82.4 (97.6) | 5.5 | 99.3 |
| 600° F. (315.6 degree Celsius) | 10 | 82.0 (97.2) | 17.1 | 97.8 |
| 650° F. (343.3 degree Celsius) | 10 | 82.1 (97.3) | 70.8 | 90.7 |

The results in Tables 3 and 4 show that dechlorination was effective in reducing the organic chloride content by up to 99.3 wt % while also maintaining the desirable trimethyl pentanes. In this example, the optimum temperature in the dechlorination reactor was in the range of 400° F. (204.4 degree Celsius) to 550° F. (287.8 degree Celsius). At an elevated temperature greater than 550° F. (287.8 degree Celsius), we found that the amount of trimethyl pentane reduced slightly and the elevated temperature caused a total chloride in the dechlorinated alkylate gasoline to be above 15 wppm.

Off-gas samples taken from the dechlorination reactor after separation in a high pressure gas/liquid separator and HCl scrubber were taken at two different yield periods and analyzed by GC for their composition, excluding nitrogen and oxygen. The results are shown below.

TABLE 5

Purity of Separated and Scrubbed Off-Gas from Dechlorination Reactor

|  | Vol % Hydrogen | Vol % C1-C3 Hydrocarbons | Vol % C4+ Hydrocarbons |
|---|---|---|---|
| Yield Period A | 95.95 | 0 | 4.05 |
| Yield Period B | 95.84 | 0.01 | 4.15 |

Both of these off-gas samples comprised greater than 90 vol % hydrogen, less than 0.05 vol % C1-C3 hydrocarbons, and between 0.5 and 9.5 vol % of C4+ hydrocarbons. The off-gas was ideal for recycling directly to the hydrogenation reactor that was integrated with this process. Recycling the off-gas containing mostly hydrogen, which was separated from the dechlorination reactor effluent, to the hydrogenation reactor used to regenerate the ionic liquid catalyst, saved significant overall process cost.

Example 7

Regeneration of Ionic Liquid Catalyst Using Pure Hydrogen vs. Off-Gas from the Dechlorination Reactor Used ionic liquid catalyst containing 5 wt % conjunct polymer was regenerated by passing the used ionic liquid catalyst through a hydrogenation reactor under hydrogen atmosphere (hydro-regeneration). Hydrogen gas with 99+ wt % purity was used. The hydro-regeneration of the used ionic liquid catalyst was performed in a hydrogenation reactor operated at 350° F. (176.7 degree Celsius), 350 psig, 5000 scf H$_2$/bbl ionic liquid catalyst, and 0.2 liquid hourly space velocity (LHSV) in the presence of a hydrogenation catalyst containing Pt and Pd. The regenerated catalyst effluent from the hydrogenation reactor was separated in a liquid/gas separator into gas and liquid streams. At these conditions, 80 wt % of the conjunct polymer in the used ionic liquid catalyst was converted to a light hydrocarbon material having a boiling point less than 475° F. (246.1 degree Celsius), and the regenerated ionic liquid catalyst contained less than 1 wt % conjunct polymer.

The pure hydrogen gas stream was switched to the lower purity off-gas from the dechlorination reactor. To compensate for the lower purity, the flow rate was increased by 10%, the temperature was raised slightly to 360° F. (182.2 degree Celsius), and the pressure was increased to 400 psig. 80 wt % conversion of the conjunct polymer, similar to what was achieved with the pure hydrogen, was achieved. The dechlorination pressure in the dechlorination reactor when dechlorinating the alkylate gasoline comprising the chloride contaminant was at least 30 psig above and within 100 psig (75 psig) of the hydrogenation pressure used in the hydrogenation reactor.

The transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible sub-generic combinations of the listed components and mixtures thereof.

It is claimed:

1. An integrated process to produce an alkylate gasoline, comprising:
   a. alkylating a mixture of hydrocarbons including isoparaffin and olefin using a chloride-containing ionic liquid catalyst in an alkylation reactor to produce the alkylate gasoline comprising a chloride contaminant;
   b. hydro-regenerating the chloride-containing ionic liquid catalyst in a hydrogenation reactor;
   c. hydro-dechlorinating the alkylate gasoline comprising the chloride contaminant in a dechlorination reactor at a dechlorination pressure that is 138 to 1207 kPa (20 to 175 psig) higher than a hydrogenation pressure used in the hydrogenation reactor, to produce a dechlorinated alkylate gasoline; and
   d. feeding an off-gas, comprising 70 to 99.9 vol.% hydrogen, from the dechlorination reactor to the hydrogenation reactor; wherein a hydrogenation catalyst used in the hydrogenation reactor and a dechlorination catalyst used in the dechlorination reactor both comprise Pt, Pd, or mixture thereof on an alumina support; wherein the off-gas requires no pre-treatment before feeding to the hydrogenation reactor; and wherein the off-gas additionally comprises from 100 to 50,000 wppm of a HCl produced during the hydro-dechlorinating.

2. The integrated process of claim 1, wherein a hydrogenation catalyst used in the hydrogenation reactor and a dechlorination catalyst used in the dechlorination reactor both comprise Pt and Pd on an alumina support.

3. The integrated process of claim 1, wherein the off-gas comprises from 90 to 99.9 vol % hydrogen.

4. The integrated process of claim 1, wherein the off-gas comprises from 0.5 to 9.5 vol % C4+ hydrocarbons.

5. The integrated process of claim 1, wherein the off-gas comprises from 0.5 to 20 vol % C4− hydrocarbons.

6. The integrated process of claim 1, wherein the off-gas comprises from 0 to 0.05 vol % C1-C3 hydrocarbons.

7. The integrated process of claim 1, wherein the dechlorination pressure is at least 30 psig above the hydrogenation pressure.

8. The integrated process of claim 1, wherein the dechlorination pressure is from 50 to 175 psig higher than the hydrogenation pressure.

9. The integrated process of claim 1, wherein the hydro-dechlorinating reduces a total halide from greater than 50 wppm in the alkylate gasoline comprising the chloride contaminant to less than 10 wppm in the dechlorinated alkylate gasoline.

10. The integrated process of claim 1, wherein the chloride contaminant comprises a C4+ organic chloride.

11. The integrated process of claim 1, wherein an HCl is produced during the hydro-dechlorinating and the HCl is recycled to the alkylation reactor.

12. The integrated process of claim 11, wherein the HCl from the dechlorination reactor is mixed with a hydrogenation HCl from the hydrogenation reactor to make a mixed HCl feed that is recycled to the alkylation reactor.

13. The integrated process of claim 1, wherein the dechlorinated alkylate gasoline retains from 97 to 100 wt % of a TMP in a C8 fraction of the alkylate gasoline comprising the chloride contaminant.

14. The integrated process of claim 1, wherein a temperature in the dechlorination reactor is maintained below an elevated temperature, wherein the elevated temperature causes a total chloride in the dechlorinated alkylate gasoline to be above 15 wppm.

15. The integrated process of claim 1, wherein a temperature in the dechlorination reactor is from 300° F. (148.9 degree Celsius) to 600° F. (315.6 degree Celsius).

16. The integrated process of claim 1, wherein a LHSV in the dechlorination reactor is from 0.5 to 20 $hr^{-1}$.

\* \* \* \* \*